(12) United States Patent
Pelc et al.

(10) Patent No.: US 9,125,570 B2
(45) Date of Patent: Sep. 8, 2015

(54) REAL-TIME TOMOSYNTHESIS GUIDANCE FOR RADIATION THERAPY

(75) Inventors: Norbert Joseph Pelc, Los Altos, CA (US); Rebecca Fahrig, Palo Alto, CA (US); Joseph Anthony Heanue, Oakland, CA (US); Edward Gerald Solomon, Menlo Park, CA (US); Brian Patrick Wilfley, Los Altos, CA (US)

(73) Assignees: The Board of Trustees of the Leland Stanford Junior University, Palo Alto, CA (US); Triple Ring Technologies, Inc., Newark, CA (US)

(*) Notice: Subject to any disclaimer, the term of this patent is extended or adjusted under 35 U.S.C. 154(b) by 500 days.

(21) Appl. No.: 13/184,482

(22) Filed: Jul. 15, 2011

(65) Prior Publication Data

US 2012/0014501 A1 Jan. 19, 2012

Related U.S. Application Data

(60) Provisional application No. 61/365,289, filed on Jul. 16, 2010.

(51) Int. Cl.
| | |
|---|---|
| *A61B 6/02* | (2006.01) |
| *G06T 11/00* | (2006.01) |
| *A61N 5/10* | (2006.01) |
| *G06T 7/00* | (2006.01) |
| *A61B 6/12* | (2006.01) |
| *A61B 6/03* | (2006.01) |
| *A61B 6/00* | (2006.01) |

(52) U.S. Cl.
CPC . *A61B 6/025* (2013.01); *A61B 6/12* (2013.01); *A61B 6/4014* (2013.01); *A61B 6/4028* (2013.01); *A61N 5/1049* (2013.01); *A61N 5/1067* (2013.01); *A61N 5/1071* (2013.01); *G06T 7/0012* (2013.01); *G06T 11/003* (2013.01); *A61B 6/032* (2013.01); *A61B 6/4007* (2013.01); *A61B 6/4241* (2013.01); *A61N 5/1065* (2013.01); *A61N 5/1069* (2013.01); *A61N 2005/1061* (2013.01)

(58) Field of Classification Search
CPC ............ A61B 6/00; A61B 6/02; A61B 6/025; A61B 6/03; A61B 6/4021; A61B 6/4028; A61N 5/1064; A61N 5/1065; A61N 5/1067; A61N 5/1071; A61N 2005/1072; G06T 7/0012; G06T 2207/10072; G06T 11/003; G06T 1/0007
USPC ........ 378/21–27, 62, 65, 68, 91, 92, 98, 98.6, 378/98.8, 98.12, 134–137, 145, 204, 205, 378/210, 901; 382/131, 307
See application file for complete search history.

(56) References Cited

U.S. PATENT DOCUMENTS

| | | | | |
|---|---|---|---|---|
| 5,870,450 | A * | 2/1999 | Khutoryansky et al. | 378/197 |
| 6,590,958 | B2 * | 7/2003 | Barber et al. | 378/98.8 |
| 6,895,076 | B2 * | 5/2005 | Halsmer et al. | 378/98.12 |
| 7,108,421 | B2 * | 9/2006 | Gregerson et al. | 378/197 |
| 7,742,570 | B2 * | 6/2010 | Yamaguchi | 378/98.12 |

(Continued)

*Primary Examiner* — Anastasia Midkiff
(74) *Attorney, Agent, or Firm* — Joseph T. Lin

(57) ABSTRACT

The present invention pertains to an apparatus and method for delivering radiation to a human patient or other mammal. A scanning electron beam x-ray source is used and the detector can be a photon counting detector. The area of the detector is less than the area of field of view in the patient. Tomosynthesis can be used to generate images and images can be produced rapidly in real time.

9 Claims, 9 Drawing Sheets

(56) References Cited

U.S. PATENT DOCUMENTS

2003/0081717 A1* 5/2003 Eppler et al. .................... 378/21
2005/0063510 A1* 3/2005 Hieronimi et al. .............. 378/65
2007/0280408 A1* 12/2007 Zhang ............................. 378/10
2010/0329413 A1* 12/2010 Zhou et al. ....................... 378/4
2011/0058647 A1* 3/2011 Star-Lack et al. ............... 378/23
2011/0080996 A1* 4/2011 Paidi et al. ...................... 378/21

* cited by examiner

REAL-TIME TOMOSYNTHESIS GUIDANCE FOR RADIATION THERAPY

RELATED U.S. APPLICATION

This application claims priority to the U.S. provisional patent application Ser. No. 61/365,289, entitled "REAL-TIME TOMOSYNTHESIS GUIDANCE FOR RADIATION THERAPY," with filing date Jul. 16, 2010.

FIELD OF THE INVENTION

The field of the present invention pertains generally to imaging using x-ray sources, including more specifically, to real-time tomosynthesis in order to guide radiation therapy.

BACKGROUND

Radiation is frequently used to treat cancer tumors. For treating localized cancers such as tumors, the goal is to maximize the radiation level at the tumor and minimize radiation damage to the rest of the body. This is achieved by irradiating the tumor with a narrow beam of radiation aimed at the tumor from many different angles so as to maximize the radiation at the tumor while sparing surrounding healthy tissue.

Prior to radiation treatment, the patient will usually receive a computed tomography (CT) scan to diagnose and locate the tumor and also to provide the anatomical information necessary to develop a treatment plan. A treatment plan consists of a series of positions for the radiation therapy source relative to the patient that will produce the desired radiation distribution centered on the tumor in the patient. Each position of the radiation therapy source may have different radiation energy levels, durations, and control of the profile of the radiation therapy beam.

It is critically important that the location of the tumor be accurately known so that the planned radiation distribution can be aligned with the tumor. If the radiation distribution is not accurately aligned with the tumor, the tumor will not receive a sufficient radiation level to damage or kill the tumor and healthy organs may receive damaging levels of radiation.

Various methods are used to image the tumor shortly before the radiation therapy source is activated.

These methods have several limitations. The image quality may be insufficient to show the tumor and its location and/or the imaging procedure may be sufficiently slow that there can be no assurance that the tumor is in its expected position when the radiation therapy source is activated some time later. The tumor may have moved due to motion of the patient or due to motion of the tumor within the body due to respiration, heartbeat, and/or peristalsis.

A radiation treatment system may have a linear accelerator radiation source and an x-ray imaging system consisting of an x-ray source and a large-area x-ray detector. These are attached to a rotating mechanical gantry. By rotating the gantry around the patient, many two-dimensional x-ray projection views through the patient can be obtained and a three-dimensional cone-beam CT image can be reconstructed showing the tumor and other anatomical landmarks.

Since the linear accelerator, x-ray source, and large-area detector are fixed to the same mechanical gantry, the location of the tumor relative to the radiation therapy beam can be readily and accurately determined. If the tumor is not in the correct position with respect to the radiation therapy beam, the table that supports the patient can be repositioned. Alternately, the linear accelerator energy pattern can be adjusted so that the modified radiation energy pattern is aligned with the tumor.

The x-ray source and large-area detector are arranged approximately at right angles to the radiation therapy beam. This is done to avoid direct radiation from the linear accelerator striking these components, which can be damaged by the high radiation levels from the linear accelerator.

This type of imaging system cannot provide the rapid imaging necessary to verify that the tumor is in the radiation therapy beam at the time of treatment. The rotation of the gantry around the patient to acquire the many two-dimensional projection images and the subsequent CT reconstruction typically takes many tens of seconds. CT has high contrast resolution and therefore usually has sufficient resolution to allow the tumor to be visualized. A single two-dimensional view has lower contrast resolution and may be unable to image the tumor with sufficient resolution to determine its location. Further, if the tumor moves approximately along the direction of the x-ray beam, this motion will likely not be detected in the image.

A multi-axis robotic positioning system can control the position of a linear accelerator and the direction of its radiation therapy beam.

Two x-ray imaging systems, each consisting of an x-ray source and a large area detector, can be arranged so that the patient is imaged from two approximately orthogonal views. This provides stereotactic views of the patient so that the location of the tumor can be determined from these two views and a previously acquired CT image.

The multi-axis robotic positioning system can adjust the position and/or direction of the radiation therapy beam so that the desired radiation pattern is aligned with tumor in the patient.

This stereotactic imaging system has several problems. The tumor may not be visible in one or both of the views. The contrast resolution may not be sufficient or the tumor may be obstructed by certain anatomy within the patient. The radiation therapy source may be between the source and detector, blocking one of the views.

What is needed is an imaging system capable of producing rapid high quality images in order to guide radiation therapy. Furthermore, the system should provide low radiation imaging.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
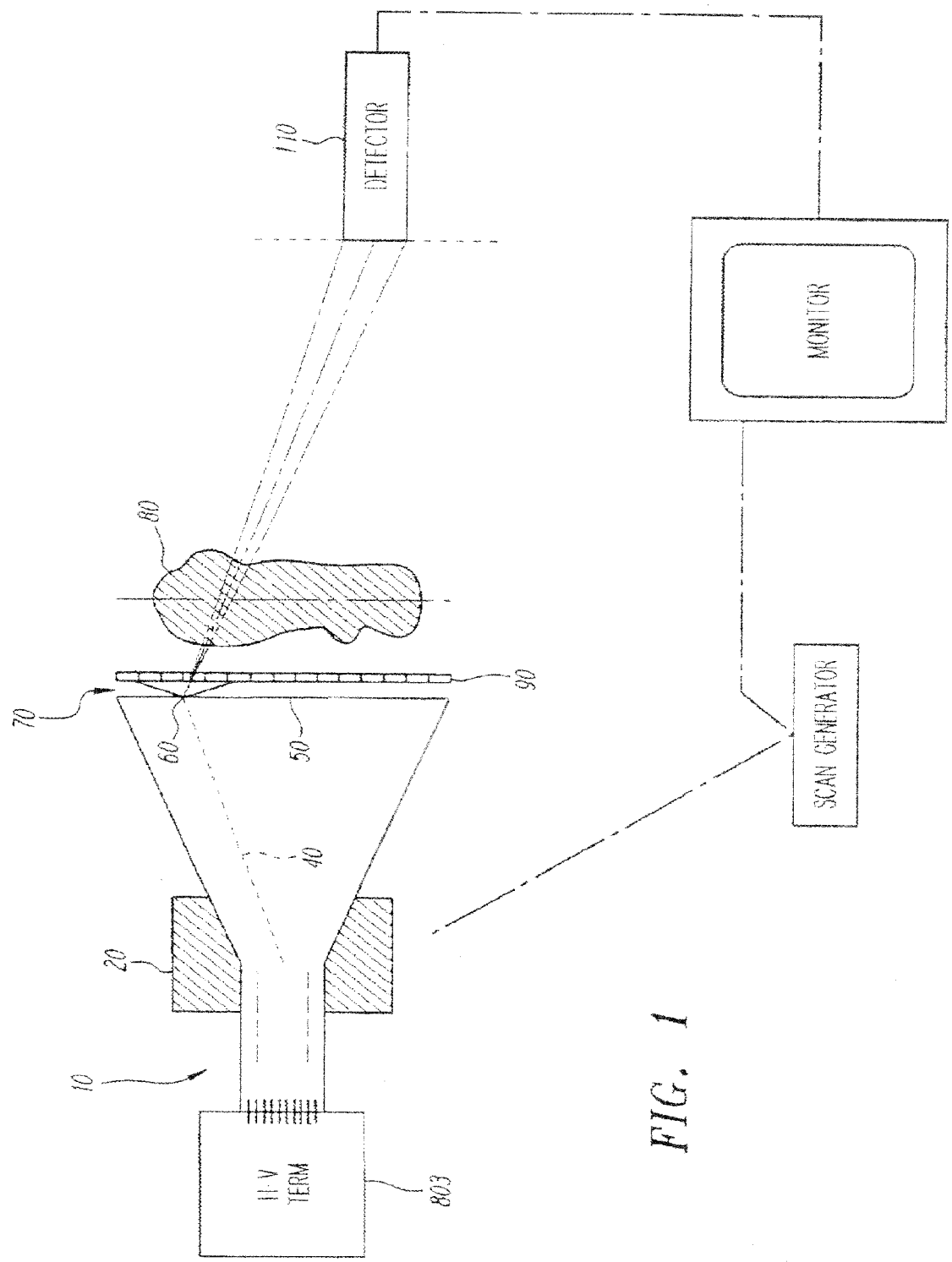
FIG. 1 is a diagram showing an exemplary x-ray imaging system of one embodiment of the present invention.

FIG. 1 is a diagram showing an exemplary x-ray imaging system of one embodiment of the present invention. Tomosynthesis can be performed using x-ray source 10 that can comprise a rapidly scanned electron-beam 40 to create an array of x-ray focal spots 60. Electrons can be produced at the cathode, accelerated by a high-voltage potential generated within high voltage terminal 803, deflected by magnetic fields produced by external electromagnets 20, and used to strike a transmission x-ray target 50 thereby producing x-ray radiation 70 from that location. A focused source collimator 90 can be utilized to limit the x-ray radiation that emerges from the source to radiation in the approximate direction of the x-ray detector 110. The extent of the pattern of x-ray source focal spots 60 on the x-ray target 50 can be larger than the maximum imaging field of view. The x-ray source 10 can produce x-ray radiation from thousands of x-ray focal spot locations in less than $1/30^{th}$ second. X-ray source 10 can be manufactured without any moving parts enhancing its beam scan speed, reliability and durability.

The x-ray detector array 110 used with this x-ray source 10 can be smaller than the maximum imaging field of view. From each x-ray source focal spot 60, a small field of view two dimensional image through the patient 80 can be obtained at the x-ray detector 110. X-ray detector 110 can be manufactured without any moving parts enhancing its image processing speed, reliability and durability. X-ray detector 110 can have an image detection speed of 100 kHz, 200 kHz, 300 kHz, 400 kHz, 500 kHz, 600 kHz, 700 kHz, 800 kHz, 900 kHz, 1 MHz, 1.2 MHz, 1.3 MHz, 1.4 MHz, 1.5 MHz, 1.6 MHz, 1.7 MHz, 1.8 MHz, 1.9 MHz, 2.0 MHz, 2.1 MHz, 2.2 MHz, 2.3 MHz, 2.4 MHz, 2.5 MHz, 2.6 MHz, 2.7 MHz, 2.8 MHz or any image detection speed between any of such values.

The many small field of view images obtained from a single scan across the x-ray target 50 can be combined using tomosynthesis algorithms in general purpose computers and/or specialized hardware to rapidly reconstruct multiple image slices at many discrete planes between the x-ray source 10 and the detector 110, in less than 0.1 seconds. Alternatively, the many small field of view images can be combined in 2.5 ms, 5 ms, 10 ms, 20 ms, 35 ms, 50 ms, 75 ms, 0.2 s, 0.5 s, 0.75 s, 1 s, 2 s, 3 s, 4 s, 5 s or any time period in between such periods or any range of time periods in between such periods. Under another embodiment of the present invention, shift and add tomosynthesis algorithm can be utilized.

This process can be repeated a short time later to provide multiple image slices repeatedly. This provides fast imaging to visualize the tumor within the patient 80 even if it is moving rapidly. The volume frame rate can be 4, 5, 6, 7, 8, 9, 10, 11, 12, 13, 14, 15, 16, 17, 18, 19, 20, 21, 22, 23, 24, 25, 26, 27, 28, 29 or 30 frames per second or any frame rate in between such frame rates or any range of frame rates in between such frame rates.

The tomosynthesis imaging system of one embodiment of the present invention can generate tomosynthesis images or multiple image slices even when x-ray source 10 is stationary or in a single position. The image slice or image slices produced by the tomosynthesis imaging system can be normal to the line between x-ray source 10 and detector 110. The image slices can also be parallel to each other. The imaging system can also generate a tomosynthesis image or an image slice without using x-rays that lie in the plane of the image.

Under an alternative embodiment of the present invention, an array of x-ray sources replaces scanning beam x-ray source 10. The array can switch very quickly between x-ray sources covering an area sufficient to provide tomosynthesis images.

The tomosynthesis imaging system of one embodiment of the present invention that uses a scanned-electron-beam x-ray source larger than the maximum image field of view and an x-ray detector smaller than the maximum image field of view exposes the patient to less radiation than a typical x-ray imaging system that uses a point x-ray source and an x-ray detector larger than the maximum image field of view.

During x-ray imaging of a patient, only about 1% of the incident x-ray radiation passes through the patient to the detector to form the image. Much of the incident radiation scatters off the patient in random directions. Scattered radiation that reaches the x-ray detector adds noise to the image, degrading the quality of the image. An x-ray imaging system with a larger area detector will intercept more scattered radiation than an x-ray imaging system with a smaller area detector. The result is that the x-ray imaging system with the smaller detector will detect less scattered radiation and have a higher image quality for the same amount of radiation to the patient. This image quality advantage can be converted to a radiation reduction advantage by lowering the input radiation to the patient.

As compared to an x-ray imaging system with a point x-ray source, an x-ray imaging system of one embodiment of the present invention that uses a larger area x-ray source distributes the x-ray radiation over a larger area on the patient's skin.

This reduces the risk of radiation damage to the patient's skin and other organs. Patient radiation can be further reduced by limiting the imaging field of view to the area around the tumor being treated. In the scanned-electron-beam x-ray source of one embodiment of the present invention, this can be readily accomplished with no moving parts by turning off the scanning electron beam for those x-ray focal spots not close to the tumor being treated. In this manner, the tomosynthesis imaging system generates tomosynthesis images with a field of view that is sufficient for visualization of at least the target volume. Alternatively, the scanning electron beam can be limited to those x-ray focal spots so that 10, 20, 30, 40, 50, 60, 70, 80, 90 or 100 pixels of the tumor being treated or any number of pixels within any such number of pixels are illuminated. The x-ray focal spots can also be further expanded to track movement of the tumor or target volume along x-axis, y-axis of the image plane or both. The x-ray focal spots can also be expanded to track movement of the tumor or target volume along x-axis, y-axis of the image plane or both along with the pixel margin described so that 10, 20, 30, 40, 50, 60, 70, 80, 90 or 100 pixels of the tumor being treated or any number of pixels within any such number of pixels are illuminated. Instead of utilizing a pixel margin, the tomosynthesis imaging system can also limit the scanning electron beam to those x-ray focal spots within a percentage outside the tumor or target volume. The percentage could be 5%, 10%, 15%, 20%, 25%, 30% or any percentage between such percentages. The tomosynthesis imaging system can also be expanded to track movement of the tumor or target volume along x-axis, y-axis of the image plane or both along with the pixel margin described so that 5%, 10%, 15%, 20%, 25%, 30% or any percentage between such percentages of additional x-ray focal spots are illuminated.

Tomosynthesis x-ray images have the attribute that a selectable section of tissue between the plane of the x-ray focal spots and the plane of the detector is imaged in sharp focus. This section of tissue is typically a planar slab. The thickness of the section may range from several cm to less than 1 mm, depending on the arrangement of the x-ray focal spots and the size and position of the x-ray detector. Alternatively, thickness of the section can be 1 mm, 2 mm, 3 mm, 4 mm, 5 mm, 6 mm, 7 mm, 8 mm, 9 mm, 1 cm, 1.5 cm, 2 cm, 2.5 cm, 3 cm, 3.5 cm, 4 cm, 4.5 cm or 5 cm or any thickness between such thicknesses or any range of thicknesses between such thicknesses. The image of objects that lie outside of this section are spatially blurred. The spatial blurring increases the further the object is located from the imaged section.

Figure 2:
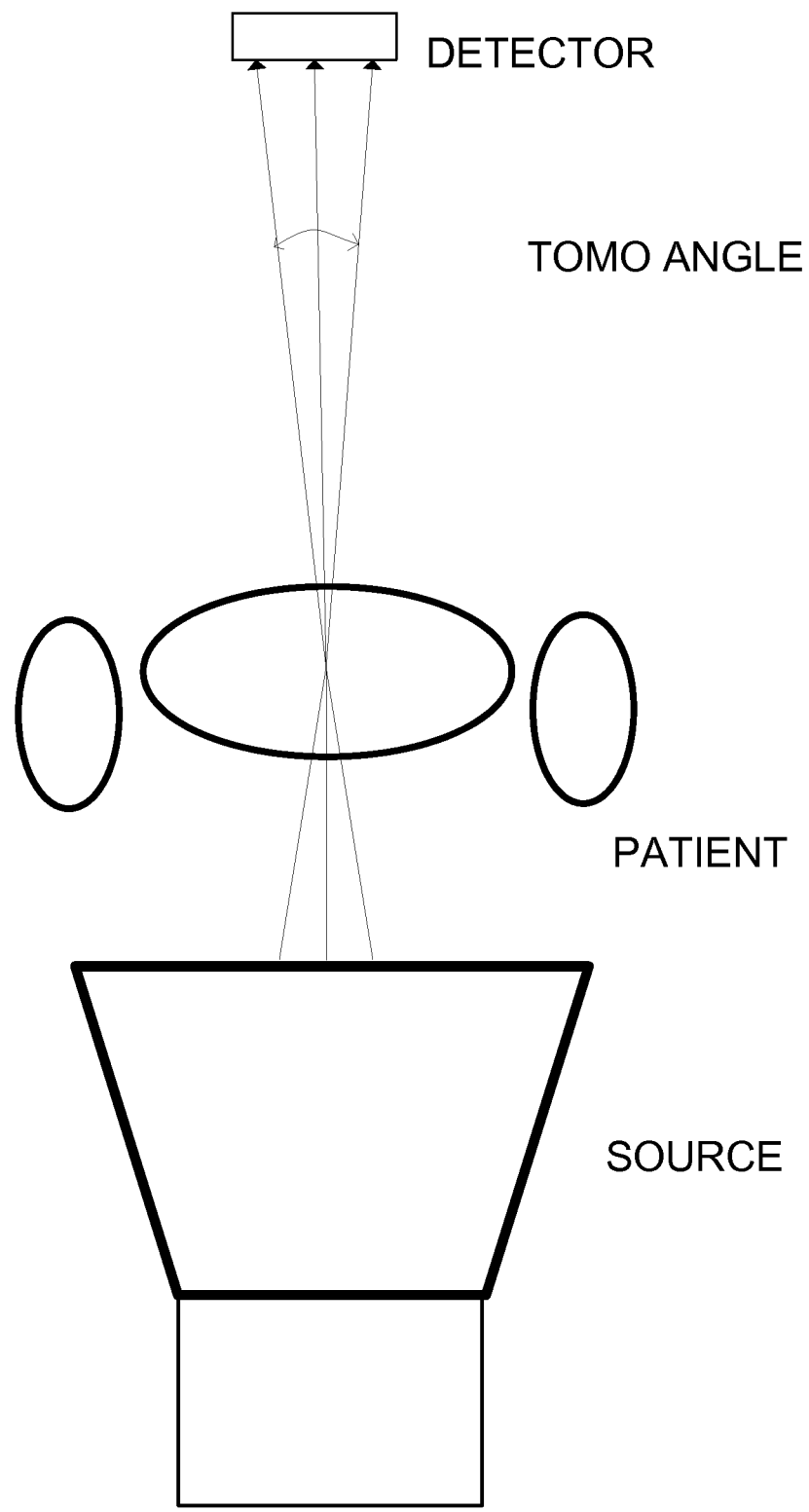
FIG. 2 is a diagram showing the tomographic angle of an exemplary imaging system of one embodiment of the present invention.

FIG. 2 is a diagram showing the tomographic angle of the imaging system of one embodiment of the present invention. The thickness of the section can be adjusted by adjusting the tomographic angle. The position of the imaging system or patient or both can be adjusted so that the tomographic angle is 2.5°, 3°, 3.5°, 4°, 4.5°, 5°, 5.5°, 6°, 6.5°, 7°, 7.5°, 8°, 8.5°, 9°, 9.5°, 10°, 10.5°, 11°, 11.5°, 12°, 12.5°, 13°, 13.5°, 14°, 14.5°, 15° or any angles in between such angles or any range of angles between such angles.

Under an alternative embodiment of the present invention, the tomographic angle is calculated as the angle between the line from a point in the image to one edge of the detector and the line from the point in the image to the opposite edge of the detector.

Tomosynthesis images of multiple sections of tissue can be generated from the same set of small field of view images obtained from a single scan of the electron beam across the x-ray target. These sections can be parallel to each other. These sections can be separated by a distance less than the thickness of the section. In this way, any object within the patient is imaged in sharp focus in at least one of the sections.

Tomosynthesis images of cancer tumors, breast tumors or treatment area margins or other tumors exhibiting sufficient soft tissue contrast can be clearer than simple two dimensional x-ray projection images. Two dimensional x-ray projection images can combine all the anatomy that the x-ray beam passes through. Clutter in the image from overlying anatomical structures reduces the clarity of any particular object such as a tumor. The tomosynthesis image can isolate a section of tissue containing the tumor and display the size, shape, and location of that tumor more clearly. Tomosynthesis can also be beneficial in imaging of tumors that take up long-dwell time contrast agents such as iodine, in that tumor contrast can be sufficient to permit visualization in tomosynthesis images with lesser amount of contrast agents.

A tomosynthesis imaging system with a fast detector and rapid image processing capabilities can provide images in real time, which can provide intra-treatment image guidance for radiation therapy treatments. Integration of the real-time tomosynthesis imaging system with a radiation therapy-producing system allows for imaging during therapy or in between radiation therapy pulses. The radiation utilized for treatment can be high-energy photons, electrons or protons. Sources of radiation can be particle accelerators, x-ray sources, or radioisotope sources.

From previous imaging studies of the patient being treated, the size and location of the tumor can be ascertained. These previous imaging studies are frequently three dimensional CT examinations performed on other CT scanners or using the CT imaging capability that may be available on the radiation treatment system of one embodiment of the present invention.

From these three dimensional CT images, expected images can be calculated for the imaging angle, section thickness, and section location of the tomosynthesis imaging system used with the radiation treatment system.

During radiation treatment, the location of the tumor can be determined automatically by comparing the actual tomosynthesis image(s) to the expected tomosynthesis image(s). For certain tumors, the location of the tumor may be sufficiently clear in the tomosynthesis images alone without the need to compare with a previously acquired CT image.

Single axis projection imaging systems lack location information in the imaging beam direction or z-axis. The tomosynthesis imaging system of one embodiment of the present invention adds information in the beam direction which can be critical to determining proper shape or direction or both of the radiation therapy beams.

In one embodiment of the present invention, the imaging system can track the target volume along x-axis or y-axis or z-axis of the image plane or any combination. The imaging system can utilize real-time segmentation of tomosynthesis reconstructions to further enhance tracking of the target volume. The tomosynthesis imaging system can accomplish segmentation by focusing on shape, contrast, edge detection or any combination. Image processing would be performed or enhanced for the pixels identified through shape, contrast, edge detection or any combination. In addition, the imaging system can utilize registration of tomosynthesis reconstructions to enhance tracking of the target volume. The imaging system can accomplish registration by comparing or matching one image against a previous image obtained either through tomosynthesis or previously acquired CT image.

The enhanced tracking of the target volume by the imaging system allows for a modified radiation therapy protocol by treating the tumor only when it is within the therapy beam.

The imaging system can maintain records of treatment so that it can track actual treatment dose delivered. The imaging system also allows for interfraction modifications to the therapy treatment plan so that adjustments can be made before, during or after each treatment stage. The imaging system can also allow for real-time tracking and treatment of target volume as it moves.

A primary advantage of having an x-ray imaging system integrated with a radiation therapy delivery system is that the imaging system can provide geometrical guidance information to the therapy system. However, certain tumors may be difficult to discern if their x-ray absorption properties are similar to those of the surrounding tissue. In these situations, fiducial markers can be implanted in the tumor to aid in the visualization of the tumor. The fiducial markers can be an object or objects of length or diameter of 0.5 mm, 1.0 mm, 1.5 mm, 2.0 mm, 2.5 mm, 3 mm, 3.5 mm, 4 mm, 4.5 mm, 5 mm or any length or diameter in between such values. The fiducials can be made of a material with atomic number of at least 22 or made of a material with density greater than aluminum or made with material with density greater than 2.7 gm per cubic cm. The fiducials can also be made with gold or stainless steel. These fiducials can be highly absorbent to x-ray radiation and are therefore readily visible in the x-ray image. Aligning the radiation therapy beam with the fiducial marker or markers also aligns the radiation therapy beam with the tumor. Such a fiducial displays significant contrast with respect to patient soft tissue when imaged with an x-ray imaging system. Further, such a fiducial is small, but visible in the x-ray image, facilitating the location of the image of the fiducial within the context of the image of the tissue of the patient.

The location of the image of a fiducial within the plane of an x-ray image can be accomplished using the imaging system. The imaging system can also classify and classify pixels according to whether the pixels do or do not show a fiducial. The imaging system can also identify and determine whether groups of pixels collectively all show a given object. The imaging system can also locate and compute coordinate values corresponding to the location groups of pixels so identified. Under one embodiment of the present invention, the system can classify through a thresholding operation, which classifies pixels in the image according to whether they have a value above or below some predetermined threshold value. The threshold value can result in the pixels corresponding to a fiducial, which due to their contrast are darker than the surrounding pixels showing patient tissue and being classified as distinct from pixels of surrounding tissue. Under an alternative embodiment of the present invention, the system can utilize magnitude-gradients and can classify pixels as being at an edge of the fiducial or a location where the pixel value changes substantially over a small number of pixels corresponding to the small size of the fiducial and identify the sharp edges of the image of the fiducial. The system can identify utilizing a connected-point algorithm which can identify pixels belonging to a fiducial if they are neighbors of one another and have the same classification. The system can locate by a centroiding operation and can compute the mean values respectively of the x-coordinates and y-coordinates of pixels belonging to a fiducial, those mean values representing approximately the center of the image of the fiducial within the context of the larger image of patient tissue.

The tomosynthesis imaging system of the present invention offers an additional capability not available to simple projection x-ray imaging systems integrated with radiation therapy delivery system. As previously described, the system provides tomosynthesis images, and those tomosynthesis images are characterized by a plane of best focus. Objects that lie near to that plane are imaged sharply and objects lying away from that plane are imaged in a blurred fashion. This characteristic of the image of an object going from blurry to sharp and back to blurry as the planes of best focus of a sequence of reconstructed images pass over the location of the object allows the system to identify the position of a fiducial along the direction corresponding to the displacement of the planes. The location a fiducial within a plane can correspond to the x- and y-coordinates of the object in the image plane. The location of the fiducial in the direction of the displacement of the planes can be described or identified as the location along the z-coordinate. Locating an object with respect to the planes of best focus of tomographic images allows the system to supply the z-coordinate in addition to the x- and y-coordinates, thus allowing the system to provide complete geometric information on the location of a fiducial to the therapy delivery system. The therapy delivery system may also use the three-dimensional location of the fiducial to modify the therapy delivered to the patient The tomosynthesis images from a scanned-electron beam x-ray source system of one embodiment of the present invention can be produced sufficiently rapidly to track the motion of the tumor due to patient motion or due to motion of the tumor within the body due to respiration, heartbeat, and/or peristalsis. The image production time can be 2.5 ms, 5 ms, 10 ms, 20 ms, 35 ms, 50 ms, 75 ms, 0.2 s, 0.5 s, 0.75 s, 1 s, 2 s, 3 s, 4 s, 5 s or any time period in between or any range of time periods in between such periods.

These rapid images of the tumor can be used to control the radiation therapy source and/or patient table to ensure that radiation therapy beam is well aligned with the tumor when the radiation therapy source is activated.

In one embodiment of the present invention, tomosynthesis imaging system can be augmented with CT data acquisition capabilities. The tomosynthesis system can collect real-time data during gantry rotation and during gantry movement. It can store data at multiple angles of rotation around the patient during radiation therapy and reconstruct one or more CT data sets from such data including volumetric CT data. The tomosynthesis system can also acquire CT data before radiation therapy treatment by rotating the gantry. This CT data can be used to augment real-time tomosynthesis data during radiation therapy treatment in order to improve real-time image quality. In addition, CT data acquired before or during radiation therapy can be combined with real-time intra-treatment tomosynthesis to provide improved estimates of delivered dose distribution.

In one embodiment of the present invention, the radiation therapy source and the patient table are stationary for the delivery of radiation at a particular angle with respect to the patient on the table. The tomosynthesis imaging system is used to enable the radiation therapy source when the tumor is in the correct position and disable the radiation therapy source when the tumor has moved out of position with respect to the radiation source. This embodiment can be utilized for the treatment of a lung tumor where the tumor moves back and forth during the patient breathing cycle. This method of enabling and disabling the radiation therapy source can be referred to as "gating" in this patent.

In another embodiment of the present invention, the patient table is stationary and the location of the tumor determined from the tomosynthesis images is used to adjust the mechanical position of the radiation therapy and/or the direction of its radiation therapy beam to keep the radiation therapy beam well aligned with the tumor as it moves. The scanned-electron-beam x-ray source system and the mechanical actuators used to reposition the radiation therapy source can be made sufficiently rapid to allow the radiation therapy beam to track the moving tumor. This method of keeping the radiation therapy source aligned with the tumor can be referred to as "dynamic radiation therapy source control".

In another embodiment of the present invention, the radiation therapy source is held stationary for the delivery of radiation at a particular angle with respect to the patient on the table. The location of the tumor determined from the tomosynthesis images is used to adjust the mechanical position of the patient table to keep the tumor well aligned with the radiation therapy beam even as the tumor moves. The mechanical actuators used to reposition the patient table can be made sufficiently rapid to keep the tumor aligned with the radiation therapy beam. This method of controlling the patient table can be referred to as "dynamic patient table control".

Under another embodiment of the present invention, the x-ray source and x-ray detector can be rotated around the patient while collecting many two dimensional images from multiple x-ray focal spots and sufficient data can be collected to reconstruct three dimensional CT images. This technique is known as IGCT (Inverse-Geometry CT). The imaging rate is limited by the rotation speed of the x-ray source and detector around the patient.

Many useful arrangements of radiation sources, scanned-electron-beam x-ray sources, and detectors are possible. The imaging system used in conjunction with a radiation therapy source may include one or more scanned-electron-beam x-ray sources and one or more x-ray detectors.

In some embodiments of the present invention, the x-ray source(s) and detector(s) can be fixed to the same mechanical positioner as the radiation source. The relative location of the x-ray source(s) and detector(s) with respect to the radiation therapy source is therefore constant and the combined tomosynthesis imaging system and radiation therapy source move in synchrony as the mechanical positioner is adjusted.

In other embodiments of the present invention, the scanned-electron-beam x-ray source(s) and detector(s) can be fixed in position and not move as the radiation therapy source and/or patient table moves.

In yet other embodiments of the present invention, the x-ray source(s) and detector(s) can be attached to one or more mechanical positioners to allow the tomosynthesis imaging system(s) to move independently of the radiation therapy source and/or the patient table.

Figure 3:
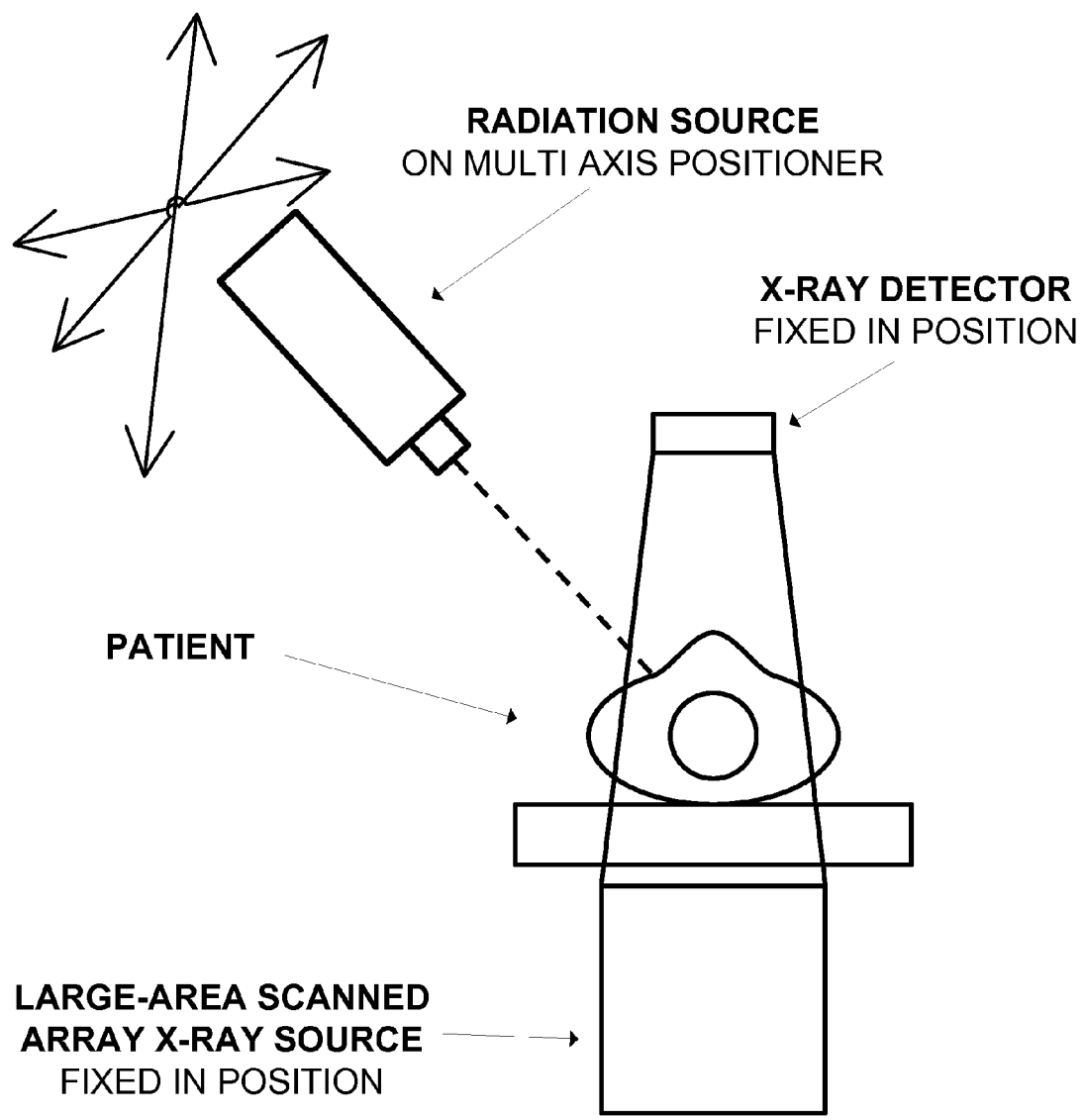
FIG. 3 is a diagram showing an exemplary x-ray imaging system of one embodiment of the present invention with a single scanned-electron-beam x-ray source and a single x-ray detector fixed in position.

FIG. 3 is a diagram showing an exemplary x-ray imaging system of one embodiment of the present invention with a single scanned-electron-beam x-ray source and a single x-ray detector fixed in position. The patient is on a table that may be fixed or moveable. A radiation therapy source is attached to a multi-axis positioner to aim its radiation therapy beam at the tumor. The multi-axis positioner can move the radiation therapy source to a series of positions as determined by the radiation treatment plan so as to concentrate the radiation delivered to the tumor while minimizing radiation to surrounding healthy tissue.

The tomosynthesis imaging system ensures that the radiation therapy beam is aligned with the tumor when the radiation therapy source is activated. Control of the radiation therapy source by the tomosynthesis imaging system may be in the form of "gating", "dynamic radiation therapy source control", "dynamic patient table control", or a combination thereof.

In this embodiment of the present invention, the detector may be located two meters from the patient, so that the radiation therapy source will not collide with detector as it moves through its series of positions. In this arrangement, the radiation therapy beam should preferably not be activated when the radiation therapy source or its multi-axis positioner is between the scanned-electron-beam x-ray source and the x-ray detector since the tomosynthesis imaging system would not be able to image the tumor to ensure that the radiation therapy beam is aligned with the tumor when the radiation therapy source is activated. Alternately the x-ray detector can be located closer the patient and the multi-axis positioner programmed so as to prevent it or the radiation therapy source from colliding with the fixed detector.

Figure 4:
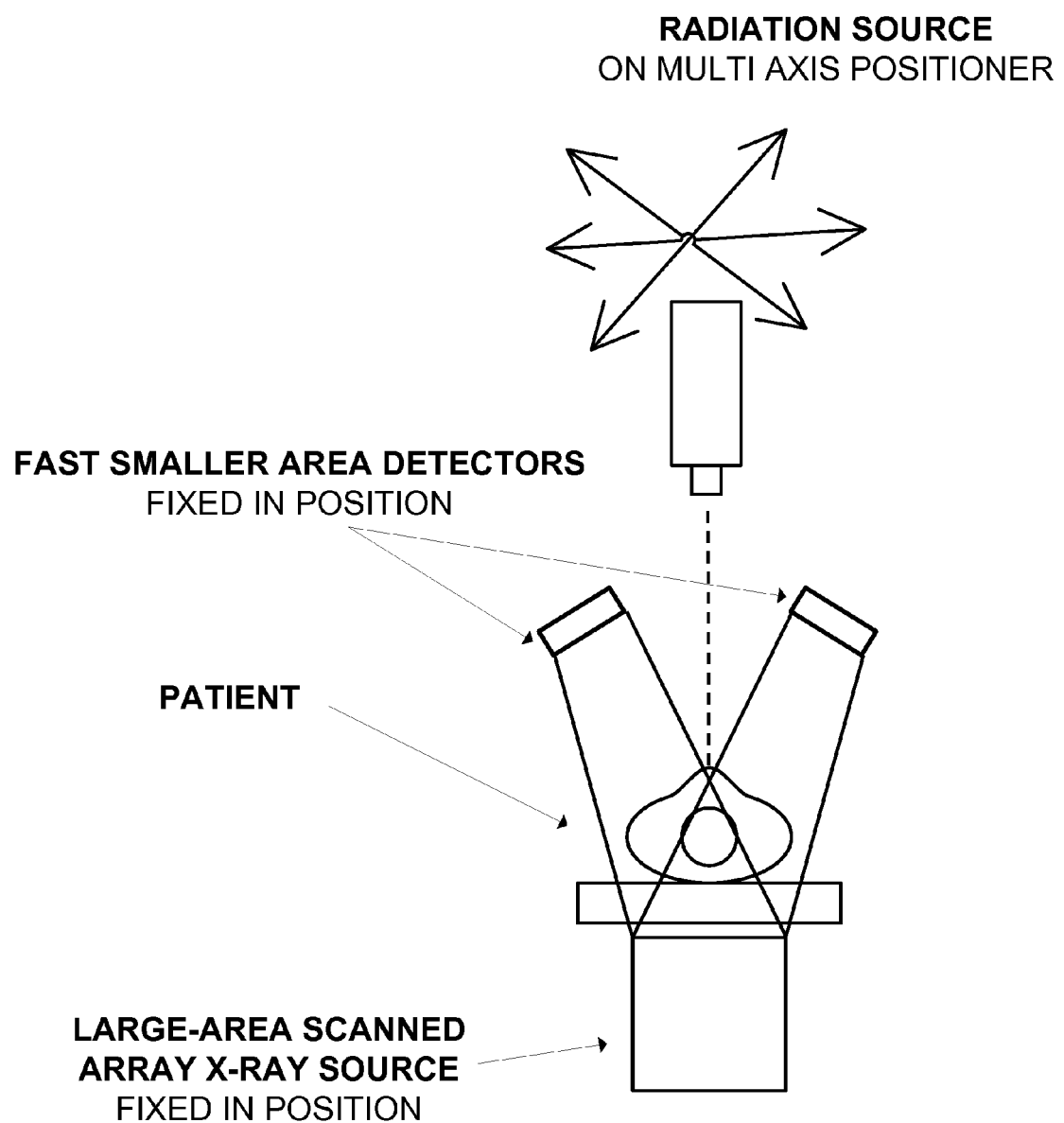
FIG. 4 is a diagram showing an exemplary x-ray imaging system of one embodiment of the present invention with a single scanned-electron-beam x-ray source and two x-ray detectors fixed in position.

FIG. 4 is a diagram showing an exemplary x-ray imaging system of one embodiment of the present invention with a single scanned-electron-beam x-ray source and two x-ray detectors fixed in position. Depending on the design of the source collimator, the scanned-electron-beam x-ray source can illuminate either detector sequentially or simultaneously as it scans its many x-ray focal spots. The patient is on a table that may be fixed or moveable. The patient should be positioned so that the tumor to be treated can be imaged by both tomosynthesis imaging systems. A radiation therapy source is attached to a multi-axis positioner to aim its radiation therapy beam at the tumor. The multi-axis positioner can move the radiation therapy source to a series of positions as determined by the radiation treatment plan so as concentrate the radiation delivered to the tumor while minimizing radiation to surrounding healthy tissue.

The use of two tomosynthesis imaging systems can provide enhanced imaging of the tumor to ensure that the radiation therapy beam is aligned with the tumor when the radiation therapy source is activated. If the image of the tumor from one of the tomosynthesis imaging systems is obscured for example, by the patient's spine or other anatomy, the image of the tumor from the other tomosynthesis imaging system may be satisfactory. If the images from both tomosynthesis imaging systems are satisfactory, the alignment accuracy of the radiation therapy beam with respect to the tumor can be improved. Control of the radiation therapy source by the tomosynthesis imaging systems may be in the form of "gating", "dynamic radiation therapy source control", "dynamic patient table control", or a combination thereof.

In this embodiment, the two x-ray detectors may be located two meters from the patient, so that the radiation therapy source will not collide with detector as it moves through its series of positions. In this arrangement, the radiation therapy beam can, if needed, be activated when the radiation therapy source or its multi-axis positioner is between the scanned-electron-beam x-ray source and one of the x-ray detectors since the unobscured tomosynthesis imaging system would still be able to image the tumor to ensure that the radiation therapy beam is aligned with the tumor when the radiation therapy source is activated. Alternately the two detectors can be located closer to the patient and the multi-axis positioner programmed so as to prevent it or the radiation therapy source from colliding with the fixed detectors.

Figure 5:
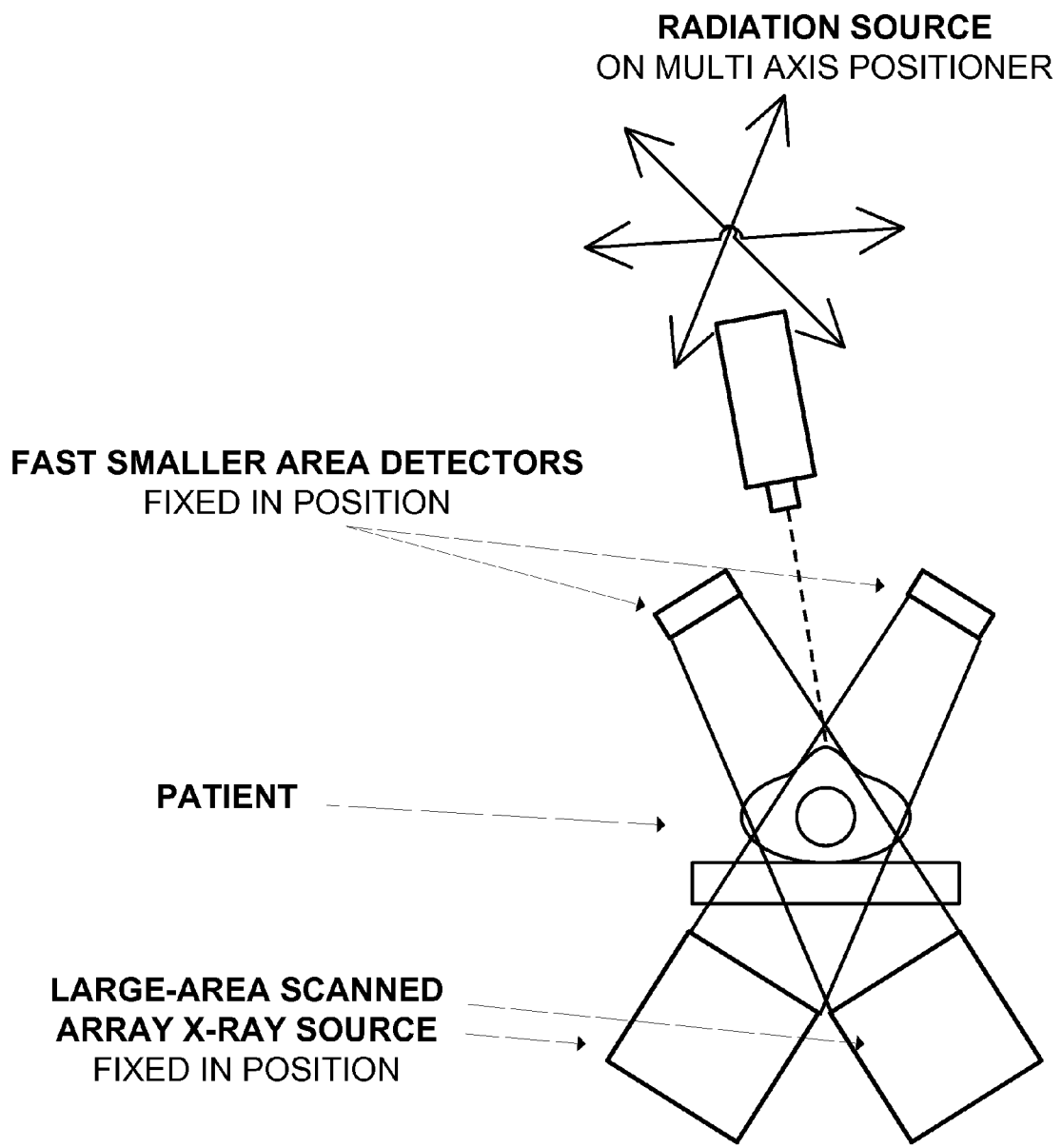
FIG. 5 is a diagram showing an exemplary x-ray imaging system of one embodiment of the present invention with two scanned-electron-beam x-ray sources and two x-ray detectors fixed in position.

FIG. 5 is a diagram showing an exemplary x-ray imaging system of one embodiment of the present invention with two scanned-electron-beam x-ray sources and two x-ray detectors fixed in position. Each scanned-electron-beam x-ray source and its associated x-ray detector form an independent tomosynthesis imaging system. Operation of the x-ray imaging system of this embodiment is similar to that described for FIG. 4. The advantage of this x-ray imaging system of this embodiment over the one described for FIG. 4 is the larger volume of intersection in the patient that can be imaged from both tomosynthesis imaging systems.

Figure 6:
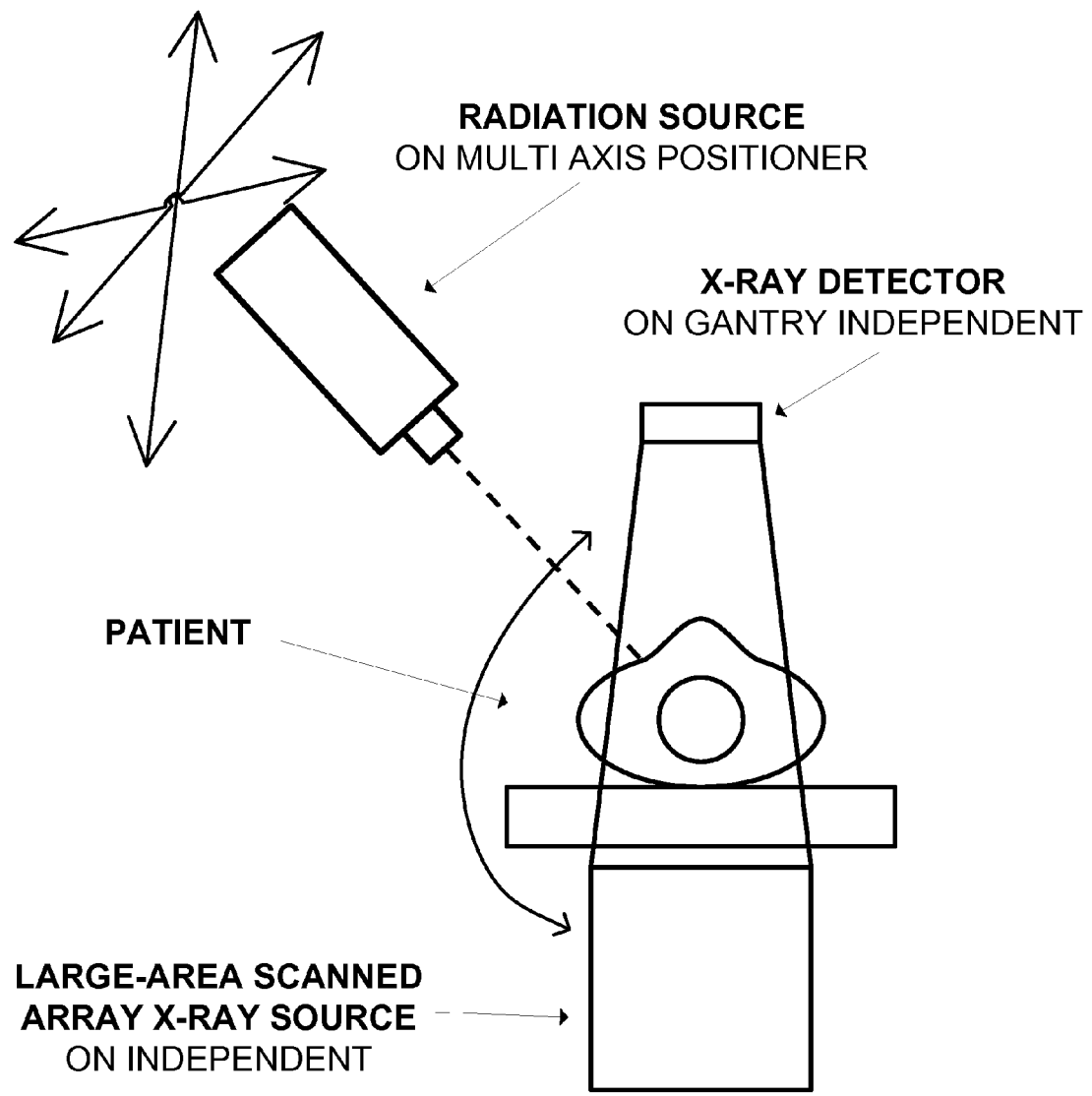
FIG. 6 is a diagram showing an exemplary x-ray imaging system of one embodiment of the present invention with a single scanned-electron-beam x-ray source and a single x-ray detector attached to an independent positioner.

FIG. 6 is a diagram showing an exemplary x-ray imaging system of one embodiment of the present invention with a single scanned-electron-beam x-ray source and a single x-ray detector attached to an independent positioner. The positioner can rotate the scanned-electron-beam x-ray source and its associated x-ray detector around the patient in a circular motion. The patient is on a table that may be fixed or moveable. A radiation therapy source is attached to a multi-axis positioner to aim its radiation therapy beam at the cancer tumor. The multi-axis positioner can move the radiation therapy source to a series of positions as determined by the radiation treatment plan so as concentrate the radiation delivered to the tumor while minimizing radiation to surrounding healthy tissue. The motion of the multi-axis positioner is independent of the motion of the positioner for the scanned-electron-beam source and associated x-ray detector.

The tomosynthesis imaging system ensures that the radiation therapy beam is aligned with the tumor when the radiation therapy source is activated. Control of the radiation therapy source by the tomosynthesis imaging system may be in the form of "gating", "dynamic radiation therapy source control", "dynamic patient table control", or a combination thereof.

The use of an independently moveable tomosynthesis imaging systems can provide enhanced imaging of the tumor to ensure that the radiation therapy beam is aligned with the tumor when the radiation therapy source is activated. If the image of the tumor from a particular position of the tomosynthesis imaging system is obscured for example by the patient's spine or other anatomy, the tomosynthesis imaging system can be repositioned so as to obtain a clear image of the tumor.

By rotating the scanning-electron-beam x-ray source and x-ray detector around the patient while collecting many two dimensional images from multiple x-ray focal spots, sufficient data can be collected to reconstruct three dimensional CT images. This technique is known as IGCT (Inverse-Geometry CT). Since the three dimensional CT images and the tomosynthesis images are obtained from the same scanned-electron-beam x-ray source and x-ray detector, the respective images are inherently spatially registered with respect to each other. The availability of these three dimensional CT images in the radiation therapy system is highly useful to ensure that a change in the patient's condition has not moved the tumor relative to other anatomical landmarks. Such a change might include an increase or decrease in patient weight over the course of several weeks of radiation treatment or the fullness of the bladder at the time of radiation treatment.

Figure 7:
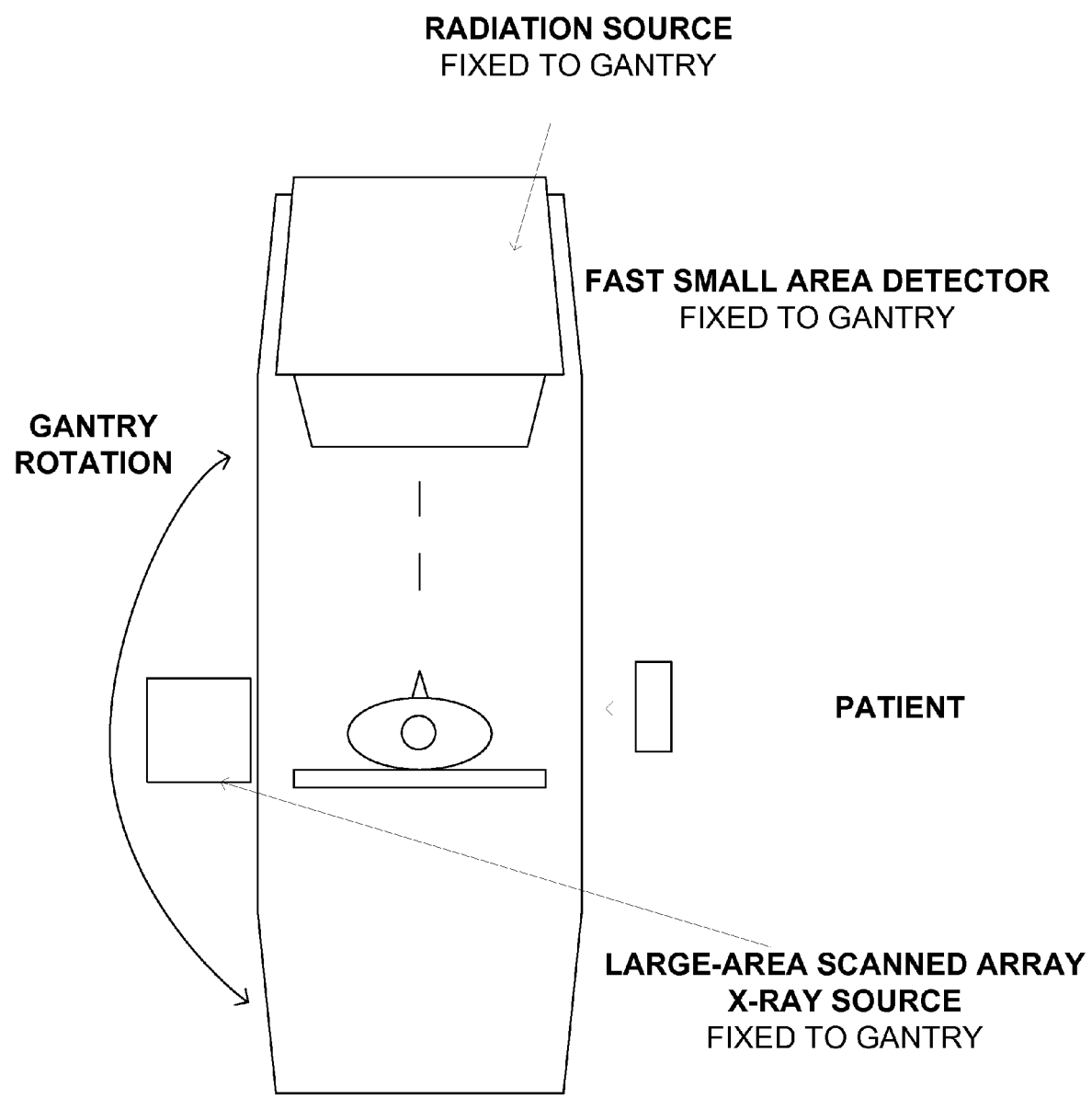
FIG. 7 is a diagram showing an exemplary x-ray imaging system of one embodiment of the present invention with a single scanned-electron-beam x-ray source and a single x-ray detector attached to the same single-axis rotational positioner as the radiation therapy source.

In this embodiment, as the radiation therapy source moves through its series of positions as required by the radiation treatment plan, the tomosynthesis imaging system can be repositioned as necessary to allow a greater range of motion by the radiation therapy source and its multi-axis positioner without collision between the radiation therapy system and the tomosynthesis imaging system FIG. 7 is a diagram showing an exemplary x-ray imaging system of one embodiment of the present invention with a single scanned-electron-beam x-ray source and a single x-ray detector attached to the same single-axis rotational positioner as the radiation therapy source. The radiation therapy beam is generally in the direction to intersect the axis of rotation and the axis of the tomosynthesis imaging system is generally orthogonal to the axis of the radiation therapy beam. This arrangement ensures that neither the scanned-electron-beam x-ray source nor the x-ray director is exposed to the direct radiation from the radiation therapy source. The patient is on a table that may be fixed or moveable. The patient is positioned so that the tumor to be treated is close to the rotational axis of the positioner.

By rotating the scanning-electron-beam x-ray source and x-ray detector around the patient while collecting many two dimensional images from multiple x-ray focal spots, sufficient data can be collected to reconstruct three dimensional CT images as previously described.

During radiation therapy treatment, the positioner moves the radiation therapy source to a series of positions on an arc as determined by the radiation treatment plan so as concentrate the radiation delivered to the tumor while minimizing radiation to surrounding healthy tissue.

The tomosynthesis imaging system ensures that the radiation therapy beam is aligned with the tumor when the radiation therapy source is activated. Control of the radiation therapy source by the tomosynthesis imaging system may be in the form of "gating", "dynamic radiation therapy source control", "dynamic patient table control", or a combination thereof.

In this embodiment, if the tissue section thickness of the tomosynthesis imaging system is greater than several mm, then the accuracy of locating the tumor along the axis of the tomosynthesis imaging may not be sufficient to ensure that the radiation therapy beam is accurately aligned with tumor.

Figure 8:
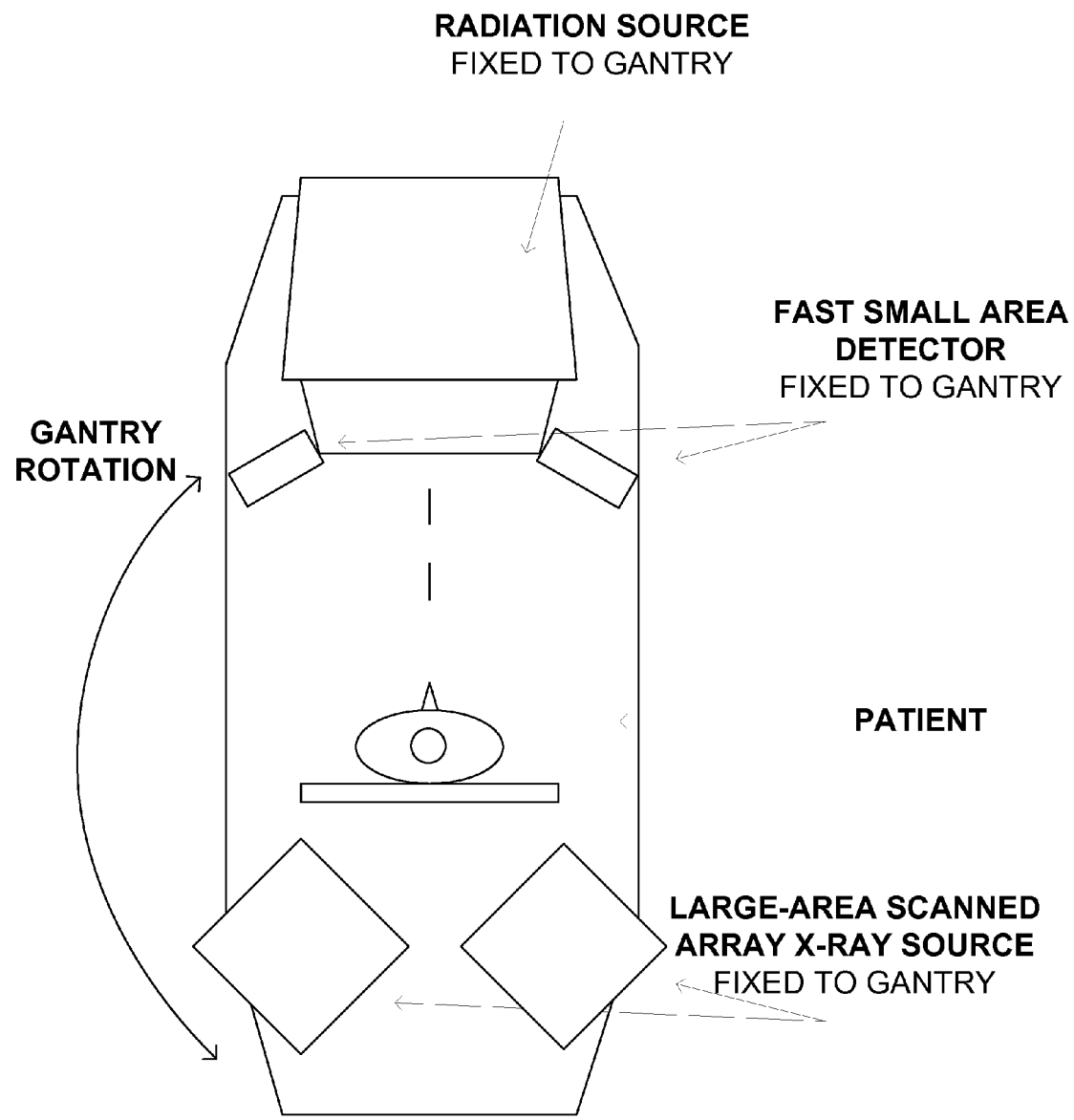
FIG. 8 is a diagram showing an exemplary x-ray imaging system of one embodiment of the present invention with two scanned-electron-beam x-ray sources and two x-ray detectors attached to the same single-axis rotational positioner as the radiation therapy source.

FIG. 8 is a diagram showing an exemplary x-ray imaging system of one embodiment of the present invention with two scanned-electron-beam x-ray sources and two x-ray detectors attached to the same single-axis rotational positioner as the radiation therapy source.

The patient is on a table that may be fixed or moveable. The patient is positioned so that the tumor to be treated is close to the rotational axis of the positioner. The arrangement of the two tomosynthesis imaging system is such that the tissue volume around the axis of rotation can be imaged by both systems.

The axes of the two tomosynthesis imaging systems each have an angle of 15, 20, 25, 30, 35, 40, 45, 50, 55, 60, 65, 70, 75 degrees with respect to the axis of the radiation therapy beam or any angle between such values or any range of angles between such values.

By rotating the scanning-electron-beam x-ray source and x-ray detector around the patient while collecting many two dimensional images from multiple x-ray focal spots, sufficient data can be collected to reconstruct three dimensional CT images as previously described.

Under an alternative embodiment of the present invention, the x-ray imaging system has only one tomosynthesis imaging system consisting of one scanning-electron-beam x-ray source and one x-ray detector. In that embodiment, the axis of the tomosynthesis imaging can be less than 30 degrees or can be 10, 15, 20, 25, 30, 35, 40 or 45 degrees with respect to the axis of the radiation therapy beam or any angle between such values or any range of angles between such values. The tissue section thickness of the tomosynthesis imaging system can be less than 5 mm or can be 15, 14, 13, 12, 11, 10, 9, 8, 7, 6, 5, 4, 3 mm or any thickness between such thicknesses or any range of thicknesses between such thicknesses to ensure the accuracy of locating the tumor along the axis of the tomosynthesis imaging will be sufficient to ensure that the radiation therapy beam is accurately aligned with tumor.

Figure 9:
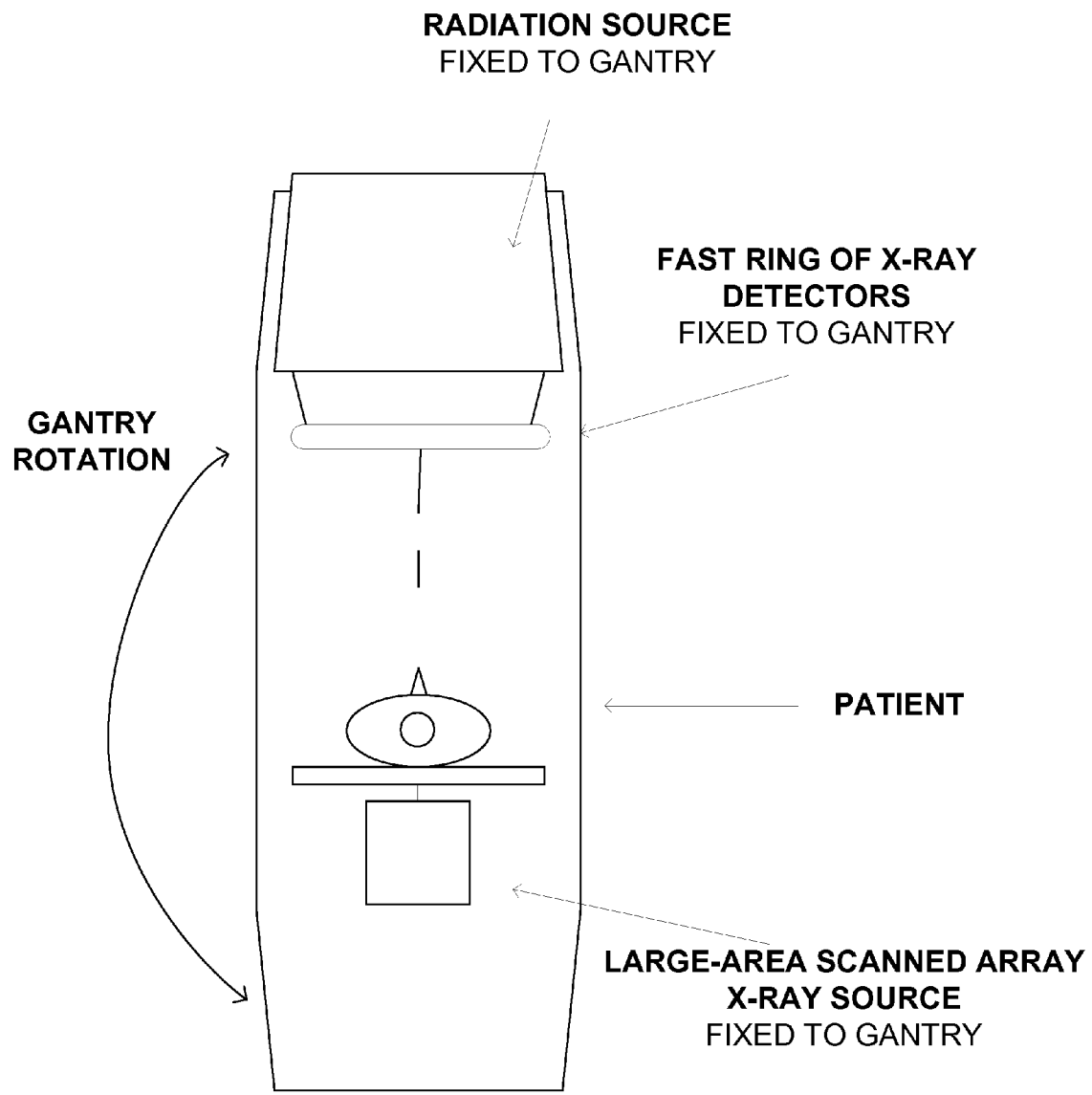
FIG. 9 is a diagram showing an exemplary x-ray imaging system of one embodiment of the present invention with a single scanned-electron-beam x-ray source attached to the same single-axis rotational positioner as the radiation therapy source.

FIG. 9 is a diagram showing an exemplary x-ray imaging system of one embodiment of the present invention with a single scanned-electron-beam x-ray source attached to the same single-axis rotational positioner as the radiation therapy source. The x-ray detector consists of multiple detector sections arranged in a ring around the radiation therapy beam. The detector sections may abut each other or have gaps between them.

The patient is on a table that may be fixed or moveable. The patient is positioned so that the tumor to be treated is close to the rotational axis of the positioner.

The tomosynthesis imaging system ensures that the radiation therapy beam is aligned with the tumor when the radiation therapy source is activated. Control of the radiation therapy source by the tomosynthesis imaging system may be in the form of "gating", "dynamic radiation therapy source control", "dynamic patient table control", or a combination thereof.

By rotating the scanning-electron-beam x-ray source and x-ray detector around the patient while collecting many two dimensional images from multiple x-ray focal spots, sufficient data can be collected to reconstruct three dimensional CT images as previously described.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for delivering radiation therapy to a mammal comprising:
    scanning an electron beam over an x-ray target to produce x-rays from a plurality of x-ray focal spots;
    directing said x-rays towards an imaging field of view and a specified object in said imaging field of view in said mammal;
    measuring amount of said x-rays striking a detector with an active imaging area smaller than an area of said imaging field of view;
    producing a first pixel representation of said object based on amount of said x-rays striking said detector from a first x-ray focal spot of said plurality of x-ray focal spots;
    producing a second pixel representation of said object based on amount of said x-rays striking said detector from a second x-ray focal spot of said plurality of x-ray focal spots;
    tracking movement of said object using said first pixel representation and said second pixel representation;
    analyzing image quality of said object in each plane of a plurality of planes;
    identifying a single plane of best focus of said object from said plurality of planes based on said analyzed image quality;
    identifying position of said object along a direction corresponding to plane displacement based on said single plane of best focus; and
    controlling radiation from a radiation therapy source towards said object.

2. The method for delivering radiation therapy of claim 1 further comprising:
    enabling said radiation therapy source when said object is aligned with said radiation therapy source.

3. The method for delivering radiation therapy of claim 1 further comprising:
    disabling said radiation therapy source when said object is not aligned with said radiation therapy source.

4. The method for delivering radiation therapy of claim 1 further comprising:
    adjusting position of said radiation therapy source to align said radiation therapy source with said object.

5. The method for delivering radiation therapy of claim 1 further comprising:
    adjusting position of said mammal to align said radiation therapy source with said object.

6. The method for delivering radiation therapy of claim 1 further comprising:
    refreshing said first pixel representation and said second pixel representation at least every 2 seconds.

7. The method for delivering radiation therapy of claim 1 further comprising:
    generating a tomosynthesis image of said object using said first pixel representation and said second pixel representation.

8. The method for delivering radiation therapy of claim 1 further comprising:
    tracking actual radiation dose delivered to said object.

9. The method for delivering radiation therapy of claim 1 further comprising:
    creating a treatment plan to deliver a specified radiation dose to said object.

* * * * *